(12) United States Patent
Bertozzi et al.

(10) Patent No.: US 10,364,242 B2
(45) Date of Patent: Jul. 30, 2019

(54) MODULATION OF N-ACYLETHANOLAMINE-HYDROLYSING ACID AMIDASE (NAAA) FOR DISEASE TREATMENT

(71) Applicant: FONDAZIONE ISTITUTO ITALIANO DI TECNOLOGIA, Genoa (IT)

(72) Inventors: Fabio Bertozzi, Genoa (IT); Tiziano Bandiera, Pavia (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 0 days.

(21) Appl. No.: 15/803,379

(22) Filed: Nov. 3, 2017

(65) Prior Publication Data
US 2019/0135802 A1    May 9, 2019

(51) Int. Cl.
*A61K 31/46* (2006.01)
*C07D 451/06* (2006.01)
*A61P 29/00* (2006.01)

(52) U.S. Cl.
CPC ............ *C07D 451/06* (2013.01); *A61P 29/00* (2018.01)

(58) Field of Classification Search
CPC ............................ A61K 31/46; C07D 401/12
USPC ........................................ 514/304; 546/130
See application file for complete search history.

(56) References Cited

U.S. PATENT DOCUMENTS

2013/0281490 A1   10/2013  Piomelli et al.

FOREIGN PATENT DOCUMENTS

WO      2009/049238 A1    4/2009

OTHER PUBLICATIONS

C.B. Merrill et al., Suppression of seizure-induced glial activation in the hippocampus using a novel N-acylethanolamine acid amidase inhibitor, Department of Anatomy and Neurobiology, University of California, Irvine, Program Poster #46.091P7, Nov. 12, 2016.
Bennett, G. et al., "A peripheral mononeuropathy in rat that produces disorders of pain sensation like those seen in man", Pain, 33(1): 87-107 (1988).
Armirotti, A. et al., "B-Lactones Inhibit N-acylethanolamine Acid Amidase by S-Acylation of the Catalytic N-Terminal Cysteine", ACS Med. Chem. Lett., 3: 422-426 (2012).
Calignano, A. et al., "Control of pain initiation by endogenous cannabinoids", Nature, 394: 277-281 (1998).
D'Agostino, G. et al., "Central administration of palmitoylethanolamide reduces hyperalgesia in mice via inhibition of NF-kB nuclear signalling in dorsal root ganglia", European Journal of Pharmacology, 613: 54-59 (2009).
Hargreaves, K. et al., "A new and sensitive method for measuring thermal nociception in cutaneous hyperalgesia", Pain, 32: 77-88 (1988).
Kemeny, L. et al., "Endogenous Phospholipid Metabolite Containing Topical Product Inhibits Ultraviolet Light-Induced Inflammation and DNA Damage in Human Skin", Skin Pharmacol Physiol, 20: 155-161 (2007).
La Rana, G., et al., "AM404, an anandamide transport inhibitor, reduces plasma extravasation in a model of neuropathic pain in rat: Role for cannabinoid receptors", Neuropharmacology, 54: 521-529 (2008).
Petracca, R. et al., "Progress in the development of B-lactams as N-Acylethanolamine Acid Amidase (NAAA) inhibitors Synthesis and SAR study of new, potent N—O-substituted derivatives", European Journal of Medicinal Chemistry, 126: 561-575 (2017).
Romeo, E. et al., "Activity-Based Probe for N-Acylethanolamine Acid Amidase", ACS Chem. Biol., 10: 2057-2064 (2015).
Speers, A. et al., "Activity-Based Protein Profiling (ABPP) and Click Chemistry (CC)-ABPP by MudPIT Mass Spectrometry", Curr Protoc Chem Biol, 1: 29-41 (2009).

*Primary Examiner* — Jeffrey H Murray
(74) *Attorney, Agent, or Firm* — Merchant & Gould P.C.

(57) ABSTRACT

Pharmaceutical compositions make up a compound acting as inhibitor of N-acylethanolamine-hydrolyzing acid amidase (NAAA), may be used for the therapeutical treatment and prevention of pain and inflammatory disorders and other disorders which benefit from the modulation of fatty acid ethanolamines, particularly palmitoylethanolamide (PEA). The compound is used in methods of inhibiting NAAA and methods of therapeutical treatment and prevention of pain and inflammation.

5 Claims, 4 Drawing Sheets

MODULATION OF N-ACYLETHANOLAMINE-HYDROLYSING ACID AMIDASE (NAAA) FOR DISEASE TREATMENT

FIELD OF THE INVENTION

The present invention relates to a novel compound acting as inhibitor of N-acylethanolamine-hydrolysing acid amidase (NAAA), which may be used for the therapeutical treatment and prevention of pain and inflammatory disorders and other disorders which benefit from the modulation of fatty acid ethanolamines, particularly palmitoylethanolamide (PEA).

The invention also relates to methods of inhibiting NAAA and to methods of therapeutical treatment and prevention of pain and inflammation and to pharmaceutical compositions comprising said compound.

BACKGROUND OF THE INVENTION

It is known that compounds which are members of the saturated fatty acid N-acylethanolamine (NAE) family have a marked anti-inflammatory activity in animal models of neurological diseases.

PEA has been shown to inhibit peripheral inflammation and mast cell degranulation and to exert antinociceptive effects in rats and mice (Calignano et al., Nature, 1998, 394, 277-281).

In addition to the pharmacological activities shown in animal models, PEA has been reported to attenuate skin inflammation in humans (Kemeny et al.; Skin Pharmacology and Physiology, 2007, 20, 155-161). PEA activates the nuclear receptor peroxisome proliferator-activated receptor alpha (PPAR-α), which modulates in turn the activity of pro-inflammatory regulators such as NF-Kb (D'Agostino G. et al., Eur. J. Pharmacol. 2009, 613, 54-9).

Sustaining PEA signalling at the PPAR-α by protecting PEA from degradation is therefore envisaged as a viable approach for the treatment of inflammatory and pain states.

PEA is a preferred substrate for N-acylethanolamine-hydrolysing acid amidase (NAAA), an enzyme that catalytically hydrolyses the NAE to ethanolamine and the corresponding fatty acid. Therefore, inhibition of NAAA is expected to decrease the inactivation of PEA and restore the levels of PEA in pathological conditions characterised by markedly reduced concentration of this signalling molecule.

Methods of treating pain and inflammation by using compounds which act as inhibitors of NAAA have been disclosed e.g. in WO2009/049238 and US 2013/0281490.

The previously reported studies support the notion that inhibition of NAAA can produce therapeutically useful effects and therefore the identification of new and potent NAAA inhibitors is needed in order to provide new therapeutical agents for the treatment of pain and inflammation.

SUMMARY OF THE INVENTION

The present invention provides the compound (endo)-3-(4-butylphenoxy)-8-[(3,5-dimethyl-1H-pyrazol-4-yl)sulfonyl]-8-azabicyclo[3.2.1.]octane (in the following ARN16186) and pharmaceutically acceptable salts thereof.

The compound of the invention has the structural formula:

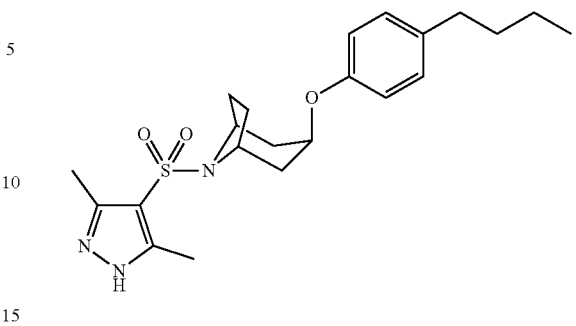

The compound of the invention has been shown to be a potent inhibitor of NAAA and may be used to treat pain and inflammatory disorders and other clinically relevant pathological states that may benefit from modulating the levels of endogenous PEA and/or other ethanolamides of long-chain fatty acids, such as N-oleylethanolamine (OEA).

In summary, ARN16186 has been found to have the following properties in-vitro:

- h-NAAA activity (fluorogenic assay): $IC_{50}=0.023\pm0.004$ μM;
- h-Acid Ceramidase (h-AC) activity: $IC_{50}>>30$ μM;
- h-Fatty Acid Amide Hydrolase (FAAH1) activity: $IC_{50}>>30$ μM
- ca. 30% recovery after 24 h in a dialysis test (partially reversible mode of inhibition);
- non-covalent mechanism of inhibition, determined by Competitive Activity Based Protein Profiling (ABPP) assay and a LC/MS recovery study.

BRIEF DESCRIPTION OF THE DRAWINGS

Features of the present invention as well as a preferred mode of use and advantages thereof will best be understood by reference to the following detailed description when read in conjunction with the accompanying drawings, wherein:

FIG. 3A: thermal hyperalgesia; FIG. 3B: tactile allodynia; FIG. 3C: mechanical hyperalgesia;

FIG. 4A: thermal hyperalgesia; FIG. 4B: tactile allodynia; FIG. 4C: mechanical hyperalgesia;

DETAILED DESCRIPTION OF THE INVENTION

Example 1: Synthesis of ARN16186

1a) tert-Butyl (exo)-3-hydroxybicyclo[3.2.1]octane-8-carboxylate

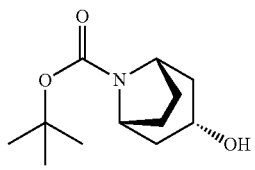

Figure 1:
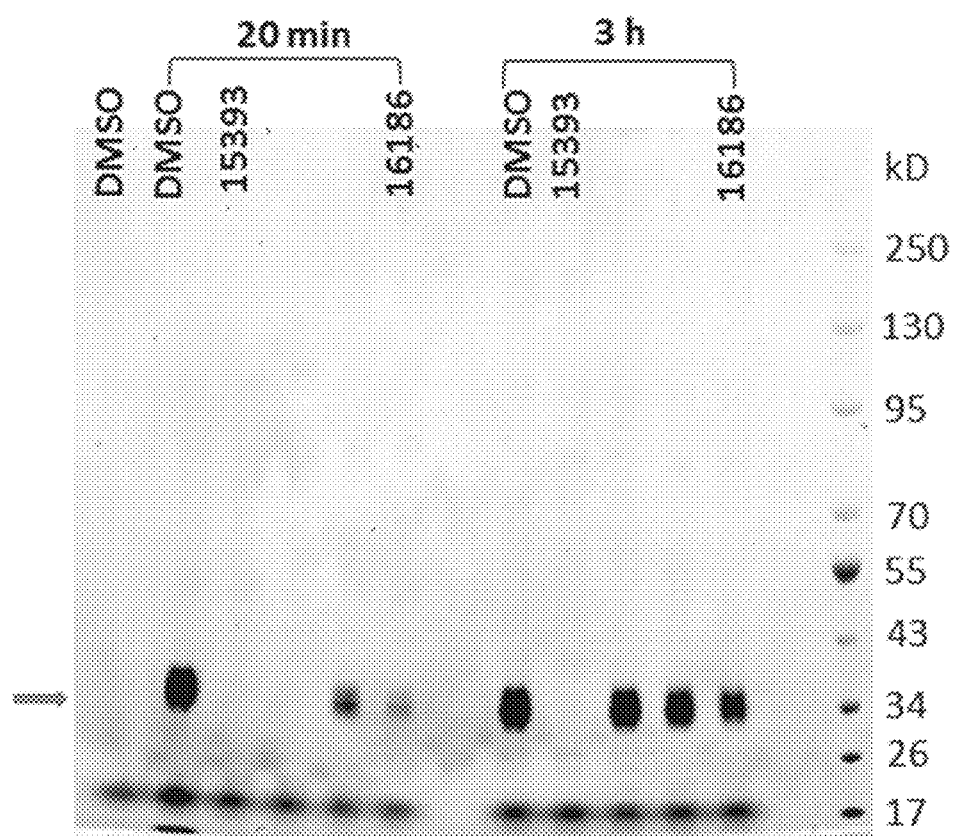
FIG. 1 is a picture showing the SDS-PAGE analysis resulting from the Competitive Activity Based Protein Profiling (ABPP): in summary, lysosomal extracts of h-NAAA overexpressing HEK293 cells were incubated with a vehicle (2% DMSO), ARN15393 (covalent h-NAAA inhibitor) or ARN16186, for 2 h before addition of probe ARN14686; a rhodamine fluorophore was inserted by a click chemistry. The arrow indicates NAAA.

tert-Butyl 3-oxo-8-azabicyclo[3.2.1]octane-8-carboxylate (0.22 g, 1.0 eq., 9.74 mmol) was dissolved in MeOH (25 mL) and the resulting solution was cooled to 0° C. Sodium borohydride (0.9 g, 2.5 eq., 24.35 mmol) was slowly added and the mixture was stirred at room temperature for 1 h. The reaction mixture was quenched with a saturated solution of $NH_4Cl$ (15 mL) and extracted with DCM (2×15 mL). The organic extracts were dried over $Na_2SO_4$ and concentrated in vacuo to furnish the crude product, which was purified by flash chromatography eluting with cyclohexane/EtOAc (0 to 60%) to give the endo product (0.12 g, 56%) and exo product (0.66 g, 30%) as white solids.

UPLC-MS: Rt. 1.95 min (TIC), ionization $ES^+$ 228 $[M+H]^+$ endo product; Rt. 1.84 min (TIC), ionization $ES^+$ 228 $[M+H]^+$ exo product.

Endo: $^1H$ NMR (400 MHz, DMSO-$d_6$): δ 4.60 (d, J=2.4 Hz, 1H), 4.03-3.95 (m, 2H), 3.94-3.87 (m, 1H), 2.20-2.07 (m, 2H), 1.93-1.70 (m, 4H), 1.69-1.57 (m, 2H), 1.39 (s, 9H).

Exo: $^1H$ NMR (400 MHz, DMSO-$d_6$): δ 4.60 (d, J=5.5 Hz, 1H), 4.09-3.97 (m, 2H), 3.95-3.83 (m, 1H), 1.79 (d, J=16.8 Hz, 4H), 1.65-1.53 (m, 2H), 1.41 (s, 9H), 1.38-1.29 (m, 2H).

1b) tert-Butyl (endo)-3-(4-butylphenoxy)-8-azabicyclo[3.2.1]octane-8-carboxylate

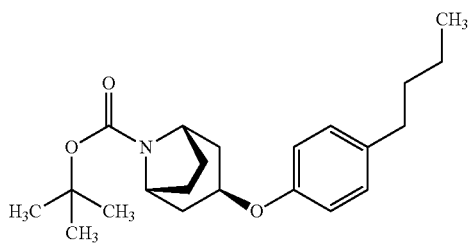

Under $N_2$ atmosphere, to a 0° C. solution of tert-butyl (exo)-3-hydroxybicyclo[3.2.1]octane-8-carboxylate (0.18 g, 1.05 eq., 0.77 mmol), 4-butylphenol (0.11 mL, 1.0 eq., 0.73 mmol), and $PPh_3$ (0.2 g, 1.05 eq., 0.77 mmol) in dry THF (4 mL) was added dropwise diisopropyl azodicarboxylate (0.15 mL, 1.05 eq., 0.77 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over $Na_2SO_4$ and concentrated in vacuo to furnish the crude product, which was purified by flash chromatography eluting with cyclohexane/EtOAc (0 to 100%) to give the pure title compound as colourless oil (0.21 g, 78%).

$^1H$ NMR (400 MHz, DMSO-$d_6$): δ 7.13-7.06 (m, 2H), 6.82-6.76 (m, 2H), 4.66 (t, J=4.9 Hz, 1H), 4.10-4.04 (m, 2H), 2.08-1.96 (m, 4H), 1.92-1.77 (m, 4H), 1.51 (tt, J=7.9, 6.4 Hz, 2H), 1.42 (s, 9H), 1.34-1.23 (m, 3H), 1.18 (t, J=7.1 Hz, 1H), 0.89 (td, J=7.3, 3.2 Hz, 3H).

1c) (endo)-3-(4-Butylphenoxy)-8-azabicyclo[3.2.1]octane trifluoroacetate

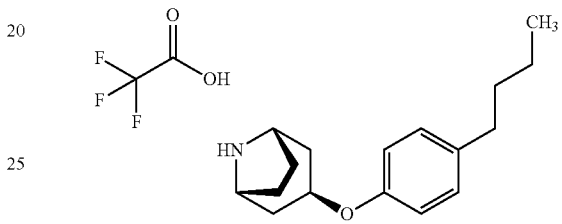

tert-Butyl (endo)-3-(4-butylphenoxy)-8-azabicyclo[3.2.1]octane-8-carboxylate (1.0 eq.) was treated at 0° C. with TFA/DCM (1:3), and the reaction stirred at room temperature for 2 h. The crude mixture was concentrated in vacuo, and re-dissolved in DCM (2 times). The desired product, as trifluoroacetate salt, was obtained in quantitative yield and it was used in the next step without any further purification.

$^1H$ NMR (400 MHz, DMSO-$d_6$): δ 8.58 (bs, J=37.3 Hz, 2H), 7.17-7.08 (m, 2H), 6.89-6.81 (m, 2H), 4.67 (t, J=4.7 Hz, 1H), 4.01-3.95 (m, 2H), 2.27-2.13 (m, 4H), 2.07-1.89 (m, 4H), 1.57-1.45 (m, 3H), 1.34-1.21 (m, 3H), 0.89 (t, J=7.4, 3.8 Hz, 3H).

1d) (endo)-3-(4-Butylphenoxy)-8-[(3,5-dimethyl-1H-pyrazol-4-yl)sulfonyl]-8-azabicyclo[3.2.1]octane (ARN16186)

(endo)-3-(4-Butylphenoxy)-8-azabicyclo[3.2.1]octane trifluoroacetate (0.21 g, 1.1 eq., 0.57 mmol) was dissolved in THF (4.0 mL). Triethylamine (0.29 mL, 4.0 eq., 2.08 mmol) was then added followed by 3,5-dimethyl-1H-pyrazole-4-sulfonyl chloride (0.1 g, 1.0 eq., 0.52 mmol). The reaction mixture was stirred at room temperature for 16 h, then quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with DCM/MeOH (0 to 2%) to give the pure title compound as white solid (0.158 g, 73%).

$^1H$ NMR (400 MHz, DMSO-$d_6$): δ 12.98 (bs, 1H), 7.31-6.86 (m, 2H), 6.86-6.60 (m, 2H), 4.61 (t, J=4.7 Hz, 1H), 4.17-3.94 (m, 2H), 2.51-2.45 (m, 2H), 2.31 (s, 6H), 2.09-1.87 (m, 6H), 1.66-1.55 (m, 2H), 1.56-1.41 (m, 2H), 1.36-1.12 (m, 2H), 0.88 (t, J=7.3 Hz, 3H).

$^{13}C$ NMR (101 MHz, DMSO-$d_6$): δ 155.11, 134.82, 129.78, 115.84, 114.93, 69.32, 55.46, 36.81, 34.36, 33.80, 28.38, 22.15, 14.22, 11.74.

Example 2: In Vitro Pharmacology

Cell Culture Conditions

Human recombinant proteins were obtained from HEK-293 stable overexpressing NAAA, AC and FAAH cell lines, respectively. Cells were grown in Dulbecco's modified Eagle medium (DMEM) containing 10% FBS, 1% penicillin/streptomycin, 1% glutamine and 500 μg/mL G418. To obtain membrane preparation cells were scraped off with cold phosphate-buffered saline (PBS) and collected by centrifugation (300×g, 7 min, 4° C.). Cell pellets were stored at −80° C. until protein preparation.

In Vitro Human NAAA and Human AC Assays

Preparation of enzyme-enriched lysate (h-NAAA and hAC). HEK-293 cells stably transfected with the human NAAA or human AC coding sequences were used as enzyme source. Cell pellets were suspended in 20 mM Tris HCl (pH 7.4) with 0.32 M sucrose, sonicated and centrifuged at 800×g for 30 min at 4° C. Supernatants were then ultracentrifuged at 12,000×g for 30 min at 4° C. Pellets were re-suspended in PBS buffer (pH 7.4) and subjected to three freeze-thaw cycles at −80° C. The suspension was finally ultracentrifuged at 105,000×g for 1 h at 4° C., supernatants were collected, protein concentration was measured and samples aliquoted and stored at −80° C. until use.

Fluorogenic h-NAAA Assay.

The assay was run in 96-well microplates (Black Opti-Plate™-96 F; PerkinElmer, Massachusetts, USA), in a total reaction volume of 200 μL. h-NAAA protein preparation (4.0 μg) was pre-incubated for 30 min with various concentrations of test compounds or vehicle control (DMSO 5%) in 100 mM citrate/phosphate buffer (pH 4.5) containing 3.0 mM DTT, 0.1% NP40 0.1%, 0.05% BSA, 150 mM NaCl. N-(4-methyl-2-oxo-chromen-7-yl)-hexadecanamide (PAMCA) was used as a substrate (2.0 μM) and the reaction carried for 50 min at 37° C. Fluorescence was measured with EnVision 2014 Multilabel Reader (PerkinElmer, Massachusetts, USA) using an excitation wavelength of 355 nm and emission 460 nm. $IC_{50}$ values were calculated by non-linear regression analysis of log [concentration]/inhibition curves using GraphPad Prism 5 (GraphPad Software Inc., CA, USA) applying a standard slope curve fitting.

Fluorogenic h-AC Assay.

The assay was run in 96-well microplates (Black Opti-Plate™-96 F; PerkinElmer, Massachusetts, USA) in a total reaction volume of 100 μL. h-AC protein preparation (2.0 μg) was pre-incubated for 10 min with various concentrations of test compounds or vehicle control (DMSO 5%) in 25 mM sodium acetate buffer (pH 4.5). N-[(1S,2R)-2-hydroxy-1-(hydroxymethyl)-4-(2-oxochromen-7-yl)oxybutyl]dodecanamide was used as substrate (5.0 μM) and the reaction carried for 3 h at 37° C., stopped with MeOH, and treated with $NaIO_4$ (fresh solution in 100 mM glycine/NaOH buffer pH 10.6) followed by 2 h incubation at 37° C. in the dark. Fluorescence was measured with EnVision 2014 Multilabel Reader (PerkinElmer, Massachusetts, USA) using an excitation wavelength of 355 nm and emission 460 nm. $IC_{50}$ values were calculated by non-linear regression analysis of log [concentration]/inhibition curves using GraphPad Prism 5 (GraphPad Software Inc., CA, USA) applying a standard slope curve fitting.

In Vitro Human FAAH Fluorescent Assay

Preparation of membrane-enriched lysate (h-FAAH). Cell pellet was re-suspended in 20 mM Tris-HCl pH 7.4, 0.32 M sucrose, disrupted by sonication (10 pulses, 5 times) and centrifuged (1000×g, 10 min, 4° C.); the collected supernatant was centrifuged at 12,000×g for 10 min at 4° C. and the supernatants were centrifuged at 100,000×g for 1 hr. The pellet was then re-suspended in PBS.

Fluorogenic h-FAAH Assay.

The fluorescent assay to measure FAAH activity was performed in 96 wells black plates: 2.5 μg of human FAAH-1 membrane preparation were pre-incubated for 50 min at 37° C., in 190 μL of assay buffer (50 mM TrisHCl pH 7.4, 0.05% Fatty acid-free BSA) with 5 μL of inhibitor or 5 μL DMSO to measure FAAH total activity. The background (no activity) samples were prepared using 190 μL of assay buffer without human FAAH-1 and 5 μL of DMSO. The reaction was then started by the addition of 5 μL of substrate (AMC arachidonoyl amide, Sigma) dissolved in DMSO and used at a final concentration of 800 nM. The reaction was carried out for 45 minutes at 37° C. and fluorescence was measured with EnVision 2014 Multilabel Reader (PerkinElmer, Massachusetts, USA) (excitation wavelength 355 nm/emission wavelength 460 nm). The concentration causing half-maximal inhibition ($IC_{50}$) was determined by non-linear regression analysis of the Log [concentration]/response curves generated with mean replicate values using a four-parameter Hill equation curve fitting with GraphPad Prism 5 (GraphPad Software Inc., CA, USA).

The results are summarized in Table 1 below.

TABLE 1

Structure, h-NAAA, h-AC (Acid Ceramidase) and h-FAAH1 (Fatty Acid Amide Hydrolase) $IC_{50}$ values of ARN16186

| Structure | Fluorogenic h-NAAA $IC_{50}$ (μM) | Fluorogenic h-AC $IC_{50}$ (μM) | Fluorogenic h-FAAH1 $IC_{50}$ (μM) |
| --- | --- | --- | --- |
| [chemical structure] | 0.023 ± 0.004 | >30 | >30 |

Example 3: Mechanism of Inhibition hNAAA Purification and Activation.

h-NAAA was produced and purified from h-NAAA overexpressing HEK293 cell line as described (*ACS Med Chem Lett* 2012, 3, 422-426). The purified enzyme was incubated in activation buffer [100 mM Sodium Phosphate/Sodium Citrate Buffer, 3 mM DL-dithiothreitol (DTT), 0.1% Triton X100, pH 4.5] for 3 h at 37° C. and the enzyme activation was checked by SDS-PAGE and Coomassie blue staining.

Competitive Activity Based Protein Profiling (ABPP) FIG. 1).

For competitive ABPP, 50 µL of lysosomal enrichment (0.5 mg/mL) from of h-NAAA-overexpressing HEK293 cell line were incubated 2 h at 37° C. with ARN16186 or covalent inhibitor ARN15393[*] at a final concentration of 20 µM (DMSO 2%). At the end of this pre-incubation time, the activity based probe undec-10-ynyl-N—[(S)-2-oxoazetidin-3-yl]carbamate (ARN14686) (*ACS Chem. Biol.* 2015, 10, 2057-2064) was added at 20 µM for 15 min or for 3.5 h at 37° C. Next, click chemistry reaction was performed by adding the following reagents at the indicated final concentrations: 100 µM Azide-PEG3-Alexa Fluor 545 (CLK-AZ109, Jena Bioscience), 1.0 mM tris(2-carboxyethyl)phosphine (TCEP) hydrochloride, 100 µM Tris [(1-benzyl-1H-1,2,3-triazol-4-yl)methyl]amine (TBTA), 1 mM $CuSO_4.5H_2O$ (*Curr Protoc. Chem. Biol.* 2009, 1, 29-41). TBTA was first dissolved in DMSO at 83.5 mM and then diluted with four volumes of t-butanol. The reaction was mixed by vortexing and incubated 2 h at 25° C. Samples (10 µL) were analysed by SDS-PAGE and gel florescence was scanned at 532 nm wavelength (Fuji Film FLA-9000 instrument).

[*] ARN15393 is the compound 4-cyclohexylbutyl N-[(2S,3S)-2-methyl-1-(4-methylsulfonylphenoxy)-4-oxoazetidin-3-yl]carbamate (cf. Eur. Jour. Med. Chem. 2017, 126, 561-575.

Figure 2:
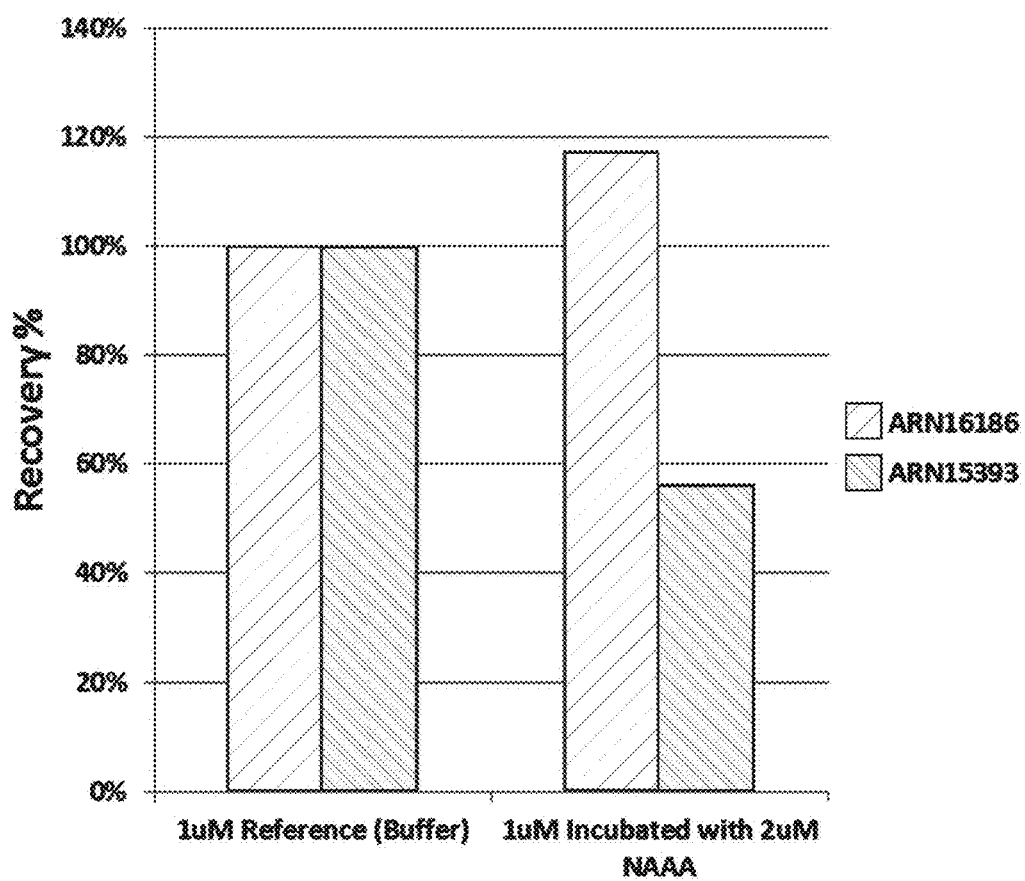
FIG. 2 is a histogram resulting from the inhibitors recovering assay: ordinate: % recovery of compounds after h-NAAA incubation; ARN16186 and covalent inhibitor ARN15393 were incubated with NAAA (right bars) or buffer alone (left bars) and quantified in supernatant after protein precipitation.

Inhibitors Recovery Assay FIG. 2).

h-NAAA (25 µL of a 2 µM solution) was incubated with ARN16186 or covalent inhibitor ARN15393 at the concentration of 1 µM in activation buffer, 2 h at 37° C. Samples were next precipitated with ten volumes of acetonitrile and centrifuged 10 min at 12000×g. The supernatants were recovered and analysed by LCMS/MS for the presence of the added compound. No-protein control samples (buffer only) were used as 100% recovery reference. Compound was detected and quantified using a Waters ACQUITY UPLC/MS TQD system consisting of a TQD (Triple Quadrupole Detector) mass spectrometer, equipped with an electrospray ionization interface. 3 uL of each sample were injected on a reversed phase column (Acquity UPLC BEH C18 2.1×50 mm, 1.7 µm particle size) and separated with a linear CH3CN gradient. Column and UPLCMS system were purchased from Waters Inc. Milford, USA. Flow rate was set 0.5 mL/min. Eluents were $A=H_2O$ and $B=CH_3CN$, both added with 0.1% formic acid. After 0.5 min at 10% B, a linear gradient of B was applied from 10% to 100% in 2 min then hold at 100% for 10 s. After the gradient, the system was reconditioned at 10% B for 1 min. Compound was quantified monitoring its MRM peak area. MS parameters were: positive ion mode; capillary 2.5 KV; cone 35V; source temperature 130° C.; cone gas 100 L/h; desolvation gas 800 L/h; desolvation temperature 400° C.

Example 4: In Vivo Pharmacology

Figure 3:
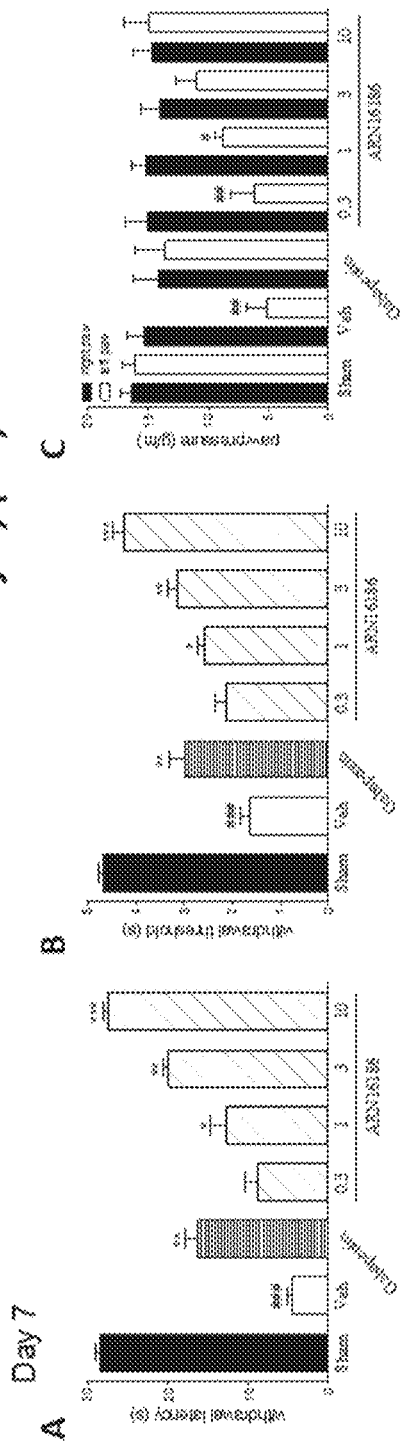
FIG. 3 shows the results of the Chronic Constriction Injury (CCI) experiments with ARN16186 administered on day 7 after left sciatic nerve ligation; pain readouts measured 2 h after dosing.
Figure 4:
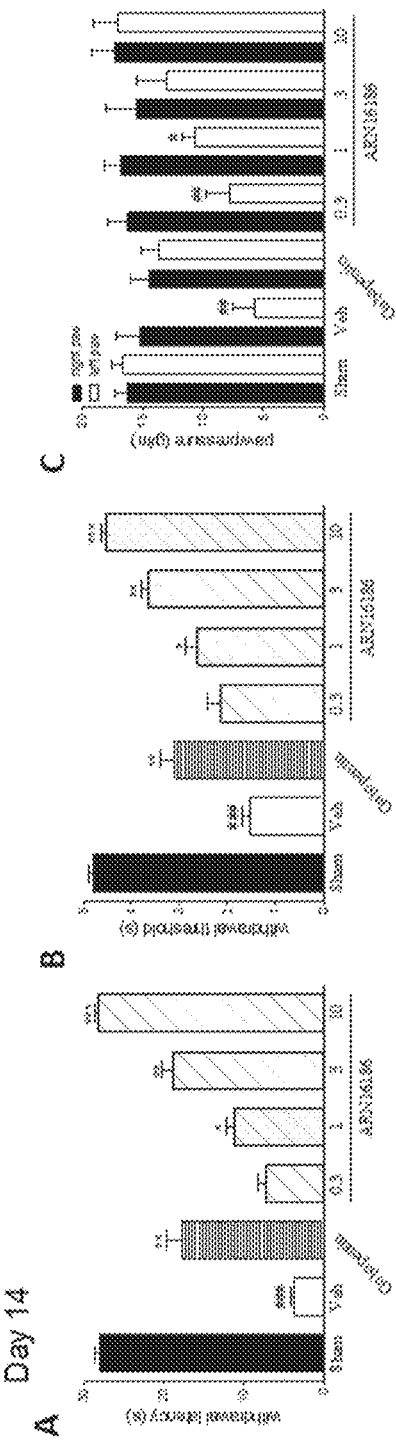
FIG. 4 shows the results of the CCI experiments with ARN16186 administered on day 14 after left sciatic nerve ligation; pain readouts were measured 2 h after dosing.
Figure 5:
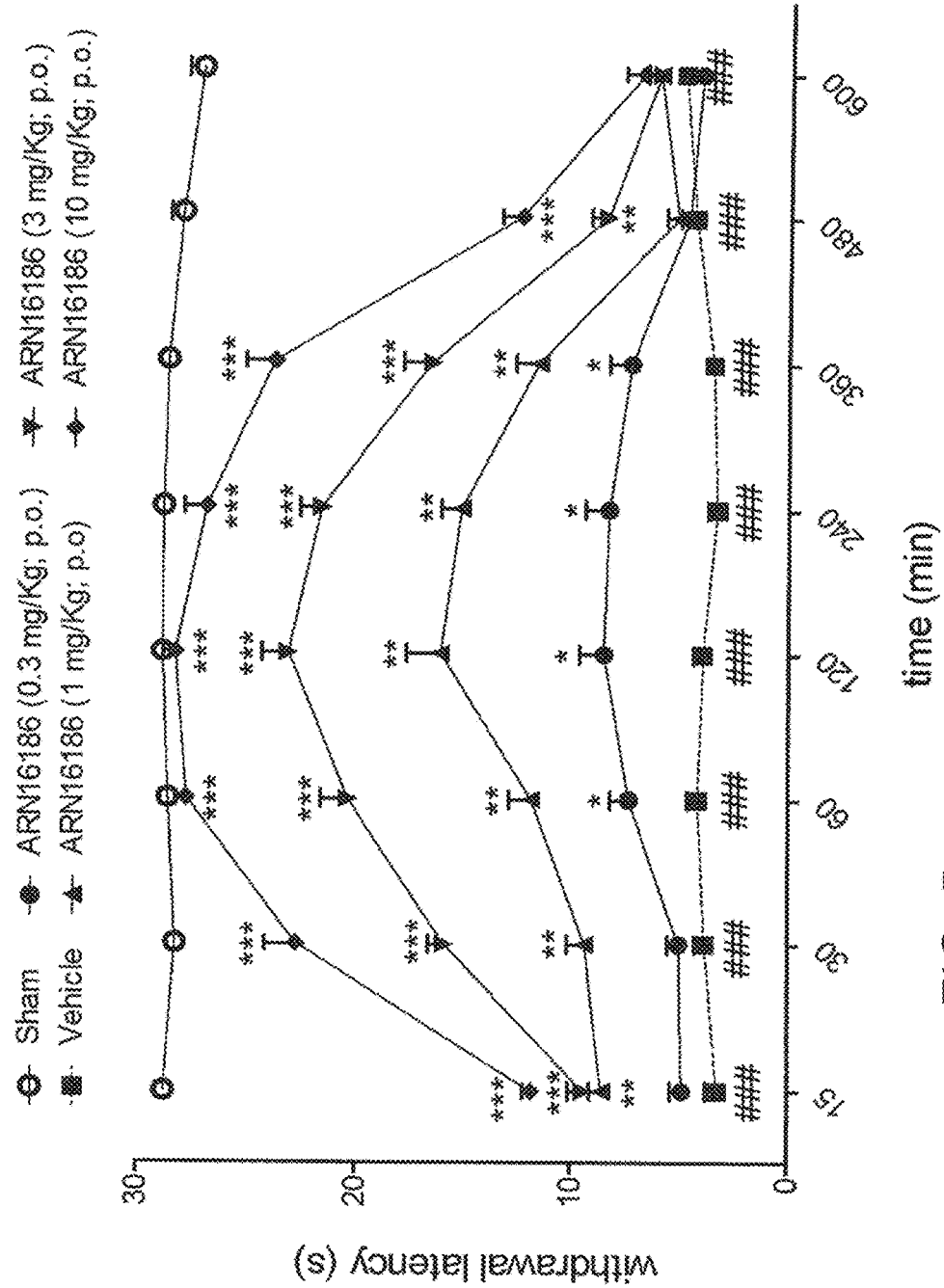
FIG. 5 is a diagram showing the results of the CCI test carried out with ARN 16186 at different dosages per os: withdrawal latency (s) versus time (minutes) after dosing.

Chronic Constriction Injury (CCI) FIGS. 3 and 4)

Sciatic nerve ligations were performed according to Bennett and Xie (Pain. 1988, 33, 87-107). Adult male CD1 mice were anesthetized with 2-3% isoflurane, and the left sciatic nerve was exposed at mid-thigh level through a small incision and tied at two distinct sites (spaced at a 2-mm interval) with a silk thread. The wound was closed with a single muscle suture and skin clips, and dusted with streptomycin. In sham-operated animals, the nerve was exposed but not tied. All experiments were performed in a quiet room, and experimenters were blinded to the treatment protocol at the time of the test.

Heat hyperalgesia was assessed by the method of Hargreaves et al. (Pain. 1988, 32, 77-88) measuring the latency to withdraw the hind paw from a focused beam of radiant heat (thermal intensity: infrared 3.0) applied to the plantar surface in a plantar test apparatus (Ugo Basile). The cutoff time was set at 30 s.

Tactile allodynia (dynamic plantar esthesiometer; Ugo Basile) was assessed as described by La Rana et al. (Neuropharmacology 2008, 54,521-529) using the Von Frey dynamic plantar aesthesiometer (DPA). Animals were placed individually in a small testing arena (20 cm×18.5 cm×13 cm) with a wire mesh floor for 5 min. The DPA device was positioned beneath the animal, so that the filament was directly under the plantar surface of the paw to be tested. When a trial was started, the device raised the filament to touch the paw and progressively increased force until the animal withdrew its paw, or until it reached a maximum of 5 g of force. The DPA automatically records the force at which the paw is withdrawn and the withdrawal latency (latency and maximum force are directly related, because the device progressively increases force until withdrawal occurs). Mechanical hyperalgesia was recorded according to the Randall Sellito measurement.

ARN16186 was then studied for its ability to alleviate established chronic pain condition (therapeutic effect). The compound was tested in the sciatic nerve chronic constriction injury (CCI) model of persistent hyperalgesia and allodynia in mice, a model that has both inflammatory and neuropathic pain components. ARN16186 (0.3, 1.0, 3.0 and 10 mg $kg^{-1}$, p.o.) was administered on day 7 and day 14, after left sciatic nerve ligation, and pain readouts were measured 2 h after dosing.

As shown in FIGS. 3 and 4, a single administration of ARN16186 was sufficient to reduce significantly both thermal hyperalgesia (FIGS. 3A and 4A), tactile allodynia (FIGS. 3B and 4B) and mechanical hyperalgesia in a dose-dependent manner, with a full effect at 10 mg $kg^{-1}$.

In view of its potent activity, the compound of the invention and pharmaceutically acceptable salts thereof can be used for the treatment of inflammatory disorders and for the treatment of pain and other clinically relevant disorders that may benefit from modulating the levels of endogenous palmitoylethanolamine, more specifically other disorders in which decreased levels of palmitoylethanolamine are associated with the disorder. Also included within the scope of the invention is the use of hydrates, solvates, racemic mixtures and single isomers of the compound of the invention.

Inflammatory disorders include acute inflammation, chronic inflammation and pain includes acute pain, acute inflammatory pain, chronic inflammatory pain and neuropatic pain. The treatment may be prophylactic or therapeutic.

Accordingly, embodiments of the invention include methods of the treatment of pain and inflammation by administering the compound of the invention, or a pharmaceutical composition thereof in a therapeutically effective amount to alleviate or treat pain and inflammation in a subject in need thereof. The treatment may be prophylactic or therapeutic. The treatment may be administered in a combination therapy with another pain reliever or anti-inflammatory agent.

The compound of the invention differs from previously reported NAAA-inhibitors for its non-covalent mechanism of enzyme-inhibition; in view of this property, possible idiosyncratic side-effects shown by covalent inhibitors of NAAA may be prevented.

The invention also provides pharmaceutical compositions of the compound of the invention or pharmaceutical acceptable salts thereof as an active ingredient and a pharmaceutically acceptable carrier and/or excipient or diluent. A pharmaceutical composition may optionally include other therapeutic ingredients.

The composition includes compositions suitable for topical, parenteral, pulmonary, nasal, rectal or oral administration.

In some embodiments, in the pharmaceutical compositions of the present invention, the active agent is generally formulated in dosage units. The dosage unit may contain from 0.1 to 1000 mg or ARN16186 or a pharmaceutically acceptable form thereof, per dosage unit for daily administration.

The invention claimed is:

1. The compound (endo)-3-(4-butylphenoxy)-8-[(3,5-dimethyl-1H-pyrazol-4-yl)sulphonyl]-8-azabicyclo[3.2.1]octane, pharmaceutically acceptable salts thereof, its hydrates, solvates and racemic mixtures.

2. A pharmaceutical composition comprising a compound according to claim 1 and a pharmaceutically acceptable carrier, excipient or diluent.

3. A method of treatment of pain and/or inflammatory disorders in which decreased levels of palmitoylethanolamine are associated with the disorder, comprising administering to a subject in need thereof a therapeutically effective amount of a compound or composition according to claim 1.

4. A method according to claim 3 for treating acute inflammation or chronic inflammation.

5. A method according to claim 3 for treatment of acute pain, acute inflammatory pain, chronic inflammatory pain or neuropathic pain.

* * * * *